United States Patent [19]

Aigner et al.

[11] Patent Number: 4,670,594
[45] Date of Patent: Jun. 2, 1987

[54] CONTINUOUS PROCESS FOR THE PREPARATION OF DIMETHYLDIALLYLAMMONIUM CHLORIDE

[75] Inventors: Rudolf Aigner, Burgkirchen; Günter Blaschke, Winhöring; Günther Müller, Burgkirchen, all of Fed. Rep. of Germany

[73] Assignee: Hoechst Aktiengesellschaft, Fed. Rep. of Germany

[21] Appl. No.: 895,182

[22] Filed: Aug. 11, 1986

[30] Foreign Application Priority Data

Aug. 13, 1985 [DE] Fed. Rep. of Germany ....... 3528985

[51] Int. Cl.$^4$ ............................................. C07C 85/04
[52] U.S. Cl. .................................................. 564/296
[58] Field of Search ........................................ 564/296

[56] References Cited

U.S. PATENT DOCUMENTS

| | | | |
|---|---|---|---|
| 2,923,701 | 2/1960 | Schuller | 564/296 |
| 3,175,008 | 3/1965 | Shapiro et al. | 564/296 |
| 3,461,163 | 8/1969 | Boothe | 564/296 |
| 3,472,740 | 10/1969 | Boothe | 564/296 |
| 4,151,202 | 4/1979 | Hunter et al. | 564/296 |

FOREIGN PATENT DOCUMENTS 136497  7/1979  Fed. Rep. of Germany .
0184052A 9/1985  Japan ................................. 564/296

Primary Examiner—Paul J. Killos
Attorney, Agent, or Firm—Connolly and Hutz

[57] ABSTRACT

In the continuous process described for the preparation of dimethyldiallylammonium chloride by reaction, with stirring, of dimethylamine, allyl chloride and alkali metal hydroxide which is dissolved in water, the reaction is carried out in at least two stirred vessels arranged in the form of a cascade. Dimethylamine and allyl chloride in the stoichiometric amount in each case and only 60 to 95 mol % of the stoichiometrically necessary amount of alkali metal hydroxide are fed to the first stirred vessel and conducted through the vessel at a temperature of 20° to 70° C. with a residence time such that the product leaving the vessel and flowing to the further vessels still contains at most 10 mol % of free amine, mol percentages being related to the molar amount of dimethylamine employed; the alkali metal hydroxide lacking in the first stirred vessel compared to the stoichiometric amount is fed continuously to the further stirred vessels mentioned and in these vessels, at a temperature of 20° to 70° C., a residence time is set such that the product leaving the vessel still contains at most 2 mol % of free amine in each case. The desired dimethyldiallylammonium chloride is obtained from the product leaving the stirred vessel cascade.

6 Claims, No Drawings

CONTINUOUS PROCESS FOR THE PREPARATION OF DIMETHYLDIALLYLAMMONIUM CHLORIDE

The invention relates to a continuous process for the preparation of dimethyldiallylammonium chloride by reaction, with stirring, of dimethylamine, allyl chloride and alkali metal hydroxide which is dissolved in water.

Dimethyldiallylammonium chloride or diallyldimethylammonium chloride (also called DADMAC below) is a useful compound, particularly in relation to the preparation of water-soluble and conductive polyammonium compounds. Thus, homo- and copolymers of DADMAC represent advantageous antistatic agents, demulsifiers, flocculents, paper auxiliaries and the like. However, the homo- and copolymers only exhibit the desired properties when very pure DADMAC has been employed for the polymerization.

A number of processes for the preparation of dimethyldiallylammonium chloride have already been described. In the known discontinuous processes, the starting compounds, i.e. dimethylamine, allyl chloride and alkali, are brought together essentially in sequence and more or less slowly, the three starting compounds being employed in a certain sequence, certain reaction temperatures and certain pHs being maintained and one or more of the starting compounds being employed in an excess and not in the stoichiometric amount, cf. U.S. Pat. Nos. 2,923,701, 3,461,163, and 4,151,202.

This complicated reaction procedure is regarded as necessary because undesired by-products, such as, particularly, allyl alcohol (by saponification or hydrolysis of allyl chloride), are otherwise formed. It is feared that allyl alcohol is formed mainly when a comparatively large amount of alkali is present in the reaction at any point in time, particularly at the beginning or in the first phase.

The starting compounds are also brought together essentially in sequence in the known continuous processes for the preparation of diallyldimethylammonium chloride, since the saponification reaction mentioned is also feared here when the alkali and allyl chloride are brought together simultaneously. Thus, in the continuous preparation process, known from DD Pat. No. 136,497 (Derwent Publication No. 70042B/39), for diallyldimethylammonium chloride using a flow reactor (flow tube), the dimethylamine and the alkali metal hydroxide solution are continuously fed in, not at the same point of the reactor at which the allyl chloride is present, but at two spatially separated points. A temperature of 10° to 30° C. and a residence time of 5 to 30 minutes are maintained in the flow tube. Although, merely because of its continuous character, this process has certain advantages compared to a non-continuous process, a number of disadvantages are, nevertheless, inherent in it. The reaction in the flow reactor does not proceed to complete quaternization, which means that the desired high yield is not attained. Since a large amount of sodium chloride, which is precipitated in solid form and is present in suspension together with the desired reaction product, is produced during the reaction, the avoidance of salt deposits in the tube reactor described is a considerable problem. Heat dissipation in the relatively short residence time which is to be maintained is difficult due to the high heat of reaction which results from the reaction. The flow reactor required for the reaction is technically complicated since it has to be fitted with special baffles, ascending flow tubes, which are connected together via brackets, and with nozzles built into the reactor. This special construction of the reactor is necessary, not least because the amine and the alkali metal hydroxide solution are to be metered in at different points of the reactor.

The invention therefore has the object of making a continuous process for the preparation of diallyldimethylammonium chloride available which supplies very pure DADMAC (without special purification operations being necessary) in a high yield when the starting compounds are used in a stoichiometric amount in each case. In addition, it should be possible to carry out the process in a technically simple apparatus and using dimethylamine even in the form of liquid gas.

The process according to the invention for the preparation of dimethyldiallylammonium chloride by reaction, with stirring, of dimethylamine, allyl chloride and alkali metal hydroxide which is dissolved in water is characterized by the reaction being carried out in at least two stirred vessels arranged in the form of a cascade, proceeding in such a manner that (a) dimethylamine and allyl chloride in the stoichiometric amount in each case and only 60 to 95 mol % of the stoichiometrically necessary amount of alkali metal hydroxide are fed simultaneously and continuously to the first stirred vessel, and, at a temperature of 20° to 70° C. and at the pressure produced, a residence time is set in this vessel such that the product leaving the vessel still contains at most 10 mol % of free amine, relative to the molar amount of dimethylamine employed, (b) the remaining amount of alkali metal hydroxide which is lacking in the first stirred vessel compared to the stoichiometric amount is fed continuously to the stirred vessels succeeding the first vessel and, at a temperature which is in the range from 20° to 70° C. and which is up to 30° C. higher than in the respective previous vessel and at the pressure produced, a residence time is set in each of these vessels such that the product leaving the vessel still contains at most 2 mol % of free amine in each case, relative to the molar amount of dimethylamine employed, this amount of free amine being held the same or smaller from vessel to vessel in the case of several subsequent stirred vessels, and (c) the desired dimethyldiallylammonium chloride is reoovered from the product leaving the stirred vessel cascade.

Since the bringing together simultaneously of the three starting compounds is advised against throughout the present state of the art for the preparation of pure DADMAC, it was surprising that very pure DADMAC is obtained using the process according to the invention, in which almost the entire stoichiometrically necessary amount of alkali metal hydroxide and the entire stoichiometric amount of dimethylamine and allyl chloride are brought together simultaneously. It has become apparent that the saponification reaction, feared in the state of the art, between allyl chloride and the alkali in the first phase of the reaction of the three starting compounds does not occur to a notable extent; this is truly an unexpected result in view of the prior publications relating to the reaction of dimethylamine, allyl chloride and alkali metal hydroxide solution. It is obviously assumed, in the entire state of the art for the preparation of DADMAC, that certain undesired reactions are preferred and proceed particularly quickly in the reaction mechanism on which the formation of DADMAC is based. As has been determined, this is not the case, precisely in the first phase of the reaction under discussion. Rather, the allyldimethylamine intermediate is obviously passed over rapidly up to a relatively high conversion rate, i.e. the quaternization (the second alkylation) quickly follows the first alkylation reaction, and it is therefore unnecessary to steer the reaction of the three starting compounds toward the intermediate mentioned by maintaining certain pH values, certain temperatures and/or by bringing the starting compounds together in a controlled manner.

The reaction under discussion can be characterized by means of the reaction equations below (NaOH is employed as alkali metal hydroxide):

$$(CH_3)_2NH + CH_2=CH-CH_2Cl \rightarrow (CH_3)_2N^{\oplus}H-CH_2-CH=CH_2Cl^{\ominus}$$

$$(CH_3)_2NH + (CH_3)_2N^{\oplus}H-CH_2-CH=CH_2Cl^{\ominus} \rightleftharpoons (CH_3)_2NH_2^{\oplus}Cl^{\ominus} + (CH_3)_2N-CH_2-CH=CH_2$$

$$(CH_3)_2N^{\oplus}H-CH_2-CH=CH_2Cl^{\ominus} + NaOH \rightarrow$$

$$(CH_3)_2N-CH_2-CH=CH_2 + NaCl + H_2O$$
$$(CH_3)_2NH_2^{\oplus}Cl^{\ominus} + NaOH \rightarrow (CH_3)_2NH + NaCl + H_2O$$
$$(CH_3)_2N-CH_2-CH=CH_2 + CH_2=CH-CH_2Cl \rightarrow (CH_3)_2N^{\oplus}(CH_2-CH=CH_2)_2Cl^{\ominus}$$

If the reaction of dimethylamine, allyl chloride and alkali (e.g. NaOH) is written as an overall equation, then this is as follows:

$$(CH_3)_2NH + 2 CH_2=CH-CH_2Cl + NaOH \rightarrow (CH_3)_2N^{\oplus}(CH_2-CH=CH_2)_2Cl^{\ominus} + NaCl + H_2O$$

It can be seen from the above reaction equations that the free amine present in the reaction mixture is the sum of dimethylamine and dimethylallylamine. It can be seen from the overall equation that the stoichiometric amounts for the reaction under discussion are 1 mol of dimethylamine, 2 mol of allyl chloride and 1 mol of alkali metal hydroxide.

Only 70 to 90% of the stoichiometrically necessary molar amount of alkali metal hydroxide are preferably fed to the first stirred vessel. Regarding the reaction temperature, the same temperature as in the first stirred vessel or a temperature which is higher by up to 30° C. than in the first stirred vessel is preferably maintained in the subsequent (to the first vessel) stirred vessels; in this case, where there are several succeeding vessels, the temperature from vessel to vessel is the same or increases in essentially identical amounts. It is particularly preferable for a temperature from 30° to 50° C. to be maintained in the first stirred vessel and a temperature from 50° to 60° C. to be maintained in the succeeding stirred vessel or vessels; in the case of several subsequent stirred vessels, the temperature from vessel to vessel is the same or increases in essentially identical amounts.

In the case of only one subsequent stirred vessel, the remaining amount of alkali metal hydroxide lacking in the first stirred vessel in comparison to the stoichiometric amount is obviously fed to the former. In the case of several subsequent (to the first stirred vessel) stirred vessels, this remaining amount is preferably fed in portions which decrease from vessel to vessel. A procedure is preferably carried out here in which 50 to 98 mol % in each case, preferably 70 to 95 mol % in each case, of the remaining amount of alkali metal hydroxide lacking in the previous stirred vessel are fed to the stirred vessels positioned between the first and the last vessel, and the entire remaining amount lacking in the previous vessel is fed to the last stirred vessel.

The product leaving the first stirred vessel preferably still contains 0.05 to 10 mol %, particularly 0.1 to 5 mol %, of free amine, mol percentages being related to the molar amount of dimethylamine employed. The product which leaves the stirred vessel or vessels which is or are located after the first stirred vessel preferably still contains 0.05 to 2 mol %, particularly 0.1 to 1 mol % of free amine, mol percentages being related to the molar amount of dimethylamine employed. In the case of several subsequent stirred vessels, the amount of free amine is kept the same in each case or is smaller from vessel to vessel; in this case, the amount of free amine preferably falls approximately evenly from vessel to vessel. The process according to the invention is preferably carried out in two or three stirred vessels which are arranged in the form of a cascade.

It follows from the abovementioned measures that, in a preferred embodiment of the process according to the invention, the reaction under discussion is carried out in two or three stirred vessels arranged in the form of a cascade, proceeding in such a manner that (a) dimethylamine and allyl chloride in the stoichiometric amount in each case and only 70 to 90 mol % of the stoichiometrically necessary amount of alkali metal hydroxide are fed simultaneously and continuously to the first stirred vessel, and, at a temperature of 30° to 50° C. and at the pressure produced, a residence time is set in this vessel such that the product leaving the vessel still contains 0.05 to 10 mol %, preferably 0.1 to 5 mol %, of free amine, (b) the remaining amount of alkali metal hydroxide lacking in the first stirred vessel in comparison to the stoichiometric amount is continuously fed to the subsequent stirred vessel or to the two subsequent stirred vessels, and, at a temperature of 50° to 60° C. and at the pressure produced, a residence time is set in each of these vessels such that the product leaving the vessel still contains 0.05 to 2 mol %, preferably 0.1 to 1 mol %, of free amine in each case, the same temperature or a higher temperature being maintained in the third vessel in comparison to the second vessel in the case of 3 stirred vessels, and 70 to 95 mol % of the remaining amount of alkali metal hydroxide lacking in the first stirred vessel being fed to the second vessel and the remaining amount still lacking in the second vessel related to the stoichiometric amount of alkali metal hydroxide being fed to the third vessel, and (c) the desired dimethyldiallylammonium chloride is recovered from the product leaving the stirred vessel cascade.

The reacting compounds, i.e. dimethylamine, allyl chloride and alkali metal hydroxide, are thus employed in the stoichiometrically necessary molar ratio, namely in the molar ratio 1:2:1 (cf. the reaction equations shown above), in the process according to the invention.

It goes without saying that the purest starting compounds possible are employed. Dimethylamine (boiling point at STP: 7° C.) can be employed as a liquid gas, i.e. 100% strength, or in the form of an aqueous solution, 20 to 50 % strength by weight solutions being preferred. Allyl chloride (boiling point at STP: 44° C.) is employed as such, since it is hardly soluble in water. Sodium hydroxide and/or potassium hydroxide is preferably employed as the alkali metal hydroxide. The concentration of the aqueous solution of the alkali metal hydroxide is 20 to 80% by weight, preferably 40 to 60% by weight. The amount (total amount) of the water employed as solvent is expediently selected so that the concentration of active compound, i.e. of DADMAC, in the product (reaction mixture) leaving the final stirred vessel (the cascade) is 40 to 75% by weight, preferably 60 to 70% by weight.

The residence time (mean residence time) in the reaction space, i.e. over all stirred vessels, for the process according to the invention is, in general, 10 to 30 hours.

Pressures from 0.2 to 2 bar arise at the reaction temperatures stated.

The free amine, i.e. the sum of dimethylamine and dimethylallylamine, can be determined, for example, by titration using 0.1 N hydrochloric acid with bromophenol blue as indicator (bromophenol blue changes from blue to yellow at pH 2.6).

It is expedient to determine the amount of hydrochloride, i.e. the sum of dimethylamine hydrochloride and dimethylallylamine hydrochloride, in each stirred vessel also (it results from the sub-stoichiometric amount of alkali metered in). This provides, for example, a check on any inaccuracies in the amount of starting compounds, such as alkali metal hydroxide, which have been metered in. This determination is carried out by titration using 0.1 N sodium hydroxide solution with thymolphthalein as indicator (thymolphthalein changes from colorless to blue at pH 9.3 to 10.5).

The product obtained in the process according to the invention is worked up, in order to obtain the desired diallyldimethylammonium chloride, by methods which are known per se. Firstly, water is distilled off (concentration), expediently in a water-pump vacuum (vacuum: about 10 to 100 mbar, temperature: about 50° C.), from the product leaving the final stirred vessel, any volatile components, such as allyl chloride, dimethylamine, allyl alcohol, dimethylallylamine and the like, being simultaneously separated off. The concentration, expediently carried out with stirring, is also carried out when the product to be worked up already displays the above-mentioned DADMAC concentrations, in order to ensure that the volatile components mentioned which are possibly present are removed. It is expedient to add a slight excess of alkali compared to the stoichiometric amount of alkali, i.e. an excess of about 0.5 mol %, to the reaction mixture to be worked up which is leaving the cascade. This excess can also be metered in as early as in the final stirred vessel. The product obtained after concentration is centrifuged (temperature: about 30° to 50° C.), to separate off the alkali metal chloride. The desired product (the reaction product) is a preferably 60 to 70% strength by weight aqueous solution of DADMAC which still contains up to about 3% of dissolved alkali metal chloride (if more concentrated solutions of DADMAC are produced during the working up procedure described, the desired concentration stated is obtained by addition of water). Complete removal of water and alkali metal chloride from the DADMAC is unnecessary because the reaction product mentioned can itself be employed for the purposes mentioned initially.

The process according to the invention has a number of advantages. The desired dimethyldiallylammonium chloride is obtained in almost quantitative yield. The slight loss of yield essentially results from the fact that some DADMAC is also removed in the centrifuging (or filtration) described for the separation of the major part of the alkali metal halide (generally sodium chloride) which is present. The aqueous DADMAC solution which is obtained no longer contains amounts of by-products which interfere with, or even prevent, the polymerization of DADMAC. The solution is, in particular, practically free of allyl alcohol and allyl chloride. This was determined using headspace gas chromatography. It is thus possible to prepare diallyldimethylammonium chloride in very high yield and in very high purity using the process according to the invention. The process according to the invention is continuous and can be carried out in stirred vessels which are simple regarding the equipment. From this results a further essential advantage, namely that the reaction under discussion can be carried out under optimum conditions regarding industrial automation, control, utilization and the maintenance of constant reaction conditions, which is obviously of great importance for a uniform product quality. A further essential advantage is that a virtually homogeneous reaction is achieved due to the high concentration in the reaction vessels of the dimethyldiallylammonium chloride formed, which displays good solution and emulsion properties for allyl chloride, solubilizing and emulsifying, this leading for example, to relatively high reaction rates. Complicated purification operations, such as, for example, purification using activated charcoal, are also unnecessary in the process according to the invention, since the desired DADMAC is obtained in a pure form.

The invention is now described in more detail with reference to examples.

EXAMPLE 1

The reaction was carried out in two stirred vessels, each with a volume of 8 $m^3$, arranged in the form of a cascade. Each of the two vessels was fitted with a stirrer, thermometer and a cooling jacket (the heat of reaction released was dissipated by means of cooling water). Per hour, the following were fed continuously into the first stirred vessel via four inlet lines: 265 kg (3.5 kmol) of allyl chloride, 78 kg (1.75 kmol) of dimethylamine and 84 kg of 50% strength by weight aqueous sodium hydroxide solution, i.e. 1.05 kmol of NaOH, and also further water, namely 86 kg. Since the stoichiometric amount of NaOH is 1.75 kmol, the 1.05 kmol of NaOH which was metered into the first stirred vessel represents only 60 mol % of the stoichiometrically necessary amount, corresponding to a stoichiometrical alkali difference of 0.7 kmol or 40 mol The remaining amount of alkali lacking in the first stirred vessel, 0.7 kmol (i.e. 56 kg of 50% strength by weight sodium hydroxide solution), was fed continuously per hour into the second stirred vessel. A temperature of 20° to 25° C. was maintained in the first stirred vessel and a temperature of 50° to 55° C. was maintained in the second vessel (a pressure of about 1.5 bar was present in the first vessel and a pressure of about 0.5 bar in the second vessel). The mean residence time over both stirred vessels was 28 hours.

The product (product mixture) leaving the first vessel contained 9 mol % of free amine and the product leaving the second vessel contained 1.8 mol %, mol percentages being related to the dimethylamine employed. (The free amine content, i.e. the sum of dimethylamine and dimethylallyl amine, was determined by titration using 0.1 N hydrochloric acid with bromophenol blue as indicator. The hydrochloride content, i.e. the sum of dimethylamine hydrochloride and dimethylallylamine hydrochloride, was also determined in the product mixture leaving the two stirred vessels; this determination was carried out by titration using 0.1 N sodium hydroxide solution with thymolphthalein as indicator, and it showed that there was no loss or excess of alkali.)

The product, which had an active compound concentration, i.e. the concentration of DADMAC, of 60% by weight, leaving the second stirred vessel was concentrated to effect further precipitation of sodium chloride, volatile components, such as free amine, allyl chloride and the like, also being removed. This was carried out using a rotary evaporator, which was operated at a temperature of 50° to 60° C. and a pressure of 80 to 100 mbar. The product mixture now present (which had a temperature of about 55° C.) was centrifuged, the sodium chloride which had been produced during the reaction and which had been additionally crystallized out by means of the concentration, being removed.

After centrifuging, the desired DADMAC was present, namely as an aqueous solution with a DADMAC content of 70% by weight and a sodium chloride content of 1.5% by weight (percentages by weight related to the aqueous solution). This solution did not contain significant amounts of impurities such as allyl chloride, allyl alcohol, free amine and amine hydrochloride.

EXAMPLE 2

The reaction was carried out in the two stirred vessels of Example 1, arranged in the form of a cascade.

Per hour, the following were fed continuously into the first stirred vessel: 353 kg (4.6 kmol) of allyl chloride, 104 kg (2.3 kmol) of dimethylamine and 129 kg of 50% strength by weight aqueous sodium hydroxide solution, i.e. 1.6 kmol of NaOH, and also further water, namely 114 kg. Since the stoichiometric amount of NaOH is 2.3 kmol, the 1.6 kmol of NaOH which was metered into the first stirred vessel represents only 70 mol % of the stoichiometrically necessary amount, corresponding to a stoichiometrical alkali difference of 0.7 kmol or 30 mol %. The remaining amount of alkali, 0.7 kmol (i.e. 56 kg of 50% strength sodium hydroxide solution), lacking in the first stirred vessel was fed continuously per hour to the second stirred vessel.

A temperature of 40° to 45° C. was maintained in the first stirred vessel and a temperature of 50° to 55° C. was maintained in the second vessel (a pressure of about 1.5 bar was present in the first vessel and a pressure of about 0.5 bar was present in the second vessel).

The mean residence time over both stirred vessels was 21 hours.

The product (product mixture) leaving the first vessel contained 4 mol % of free amine and the product leaving the second vessel contained 1 mol %, mol percentages being related to the dimethylamine employed.

The product leaving the second stirred vessel had an active compound concentration of 60% by weight and was worked up as in Example 1.

An aqueous solution which was free from contaminants and which contained 70% by weight of DADMAC and 1.5% by weight of sodium chloride was obtained.

EXAMPLE 3

The reaction was carried out in the two reaction vessels of Example 1 which were arranged in the form of a cascade.

Per hour, the following were fed continuously into the first stirred vessel: 265 kg (3.5 kmol) of allyl chloride, 78 kg (1.75 kmol) of dimethylamine and 111 kg of 50% strength aqueous sodium hydroxide solution, i.e. 1.4 kmol of NaOH, and also further water, namely 86 kg. Since the stoichiometric amount of NaOH is 1.75 kmol, the 1.4 kmol of NaOH metered into the first stirred vessel represents only 80 mol % of the stoichiometrically necessary amount, corresponding to a stoichiometrical alkali deficiency of 0.35 kmol or 20 mol %. The remaining amount of alkali, 0.35 kmol (i.e. 29 kg of 50% strength sodium hydroxide solution), lacking in the first stirred vessel was fed continuously per hour to the second stirred vessel.

A temperature of about 50° C. was maintained in the first stirred vessel and a temperature of about 50° C. was also maintained in the second vessel (a pressure of about 1.5 bar was present in the first vessel and a pressure of about 0.5 bar was present in the second vessel).

The mean residence time over both stirred vessels was 28 hours.

The product (product mixture) leaving the first vessel contained 0.3 mol % of free amine and the product leaving the second vessel contained 0.1 mol %, mol percentages being related to the dimethylamine employed.

The product leaving the second stirred vessel had an active compound concentration of 60% by weight and was worked up as in Example 1.

An aqueous solution which was free of contaminants and had a DADMAC content of 70% by weight and a sodium chloride content of 1.5% by weight was obtained.

EXAMPLE 4

The reaction was carried out in three reaction vessels, each with a volume of 8 $m^3$, arranged in the form of a cascade. Each of the three vessels was fitted with a stirrer, a thermometer and a cooling jacket (the heat of reaction released was dissipated by means of cooling water).

Per hour, the following were fed continuously into the first stirred vessel via four inlet lines: 662 kg (8.6 kmol) of allyl chloride, 195 kg (4.3 kmol) of dimethylamine and 258 kg of 40% strength by weight aqueous sodium hydroxide solution, i.e. 2.6 kmol of NaOH, and also further water, namely 128 kg. Since the stoichiometric amount of NaOH is 4.3 kmol, the 2.6 kmol of NaOH which was metered into the first stirred vessel represents only 60 mol % of the stoichiometrically necessary amount, corresponding to a stoichiometric alkali deficiency of 1.7 kmol or 40 mol %. 70%, i.e. 1.2 kmol of NaOH, of the remaining amount of alkali, 1.7 kmol, lacking in the first stirred vessel were fed continuously per hour to the second stirred vessel and the remaining amount which was still lacking in the second stirred vessel compared to the stoichiometric amount of NaOH was fed continuously per hour to the third reaction vessel.

A temperature of 20° to 25° C. was maintained in the first stirred vessel, a temperature of 40° to 45° C. was maintained in the second vessel and a temperature of 55° to 60° C. was maintained in the third vessel (a pressure of about 2.0 bar was present in the first vessel, a pressure of about 1.5 bar was present in the second vessel and a pressure of about 0.5 bar was present in the third vessel).

The mean residence time over the three stirred vessels was 19 hours.

The product (product mixture) leaving the first vessel contained 9 mol % of free amine, the product leaving the second vessel contained 2 mol % and the product leaving the third vessel contained 1 mol %, mol percentages being related to the dimethylamine employed. (The free amine content, that is the sum of dimethylamine and dimethylallylamine, was determined as in Examples 1 to 3. The amount of hydrochloride, i.e. the sum of dimethylamine hydrochloride and dimethylallylamine hydrochloride, was also determined in the product mixture leaving the three stirred vessels; this determination was carried out as in Examples 1 to 3 and showed that there was no loss or excess of alkali.)

The product leaving the third reaction vessel had an active compound concentration of 60% by weight and was worked up as in Examples 1 to 3.

An aqueous solution which was free of contaminants and had a DADMAC content of 70% by weight and a sodium chloride content of 1.5% by weight was obtained.

EXAMPLE 5

The reaction was carried out in the three reaction vessels of Example 4 arranged in the form of a cascade.

Per hour, the following were fed continuously into the first stirred vessel: 530 kg (6.9 kmol) of allyl chloride, 156 kg (3.45 kmol) of dimethylamine and 259 kg of 40% strength by weight aqueous sodium hydroxide solution, i.e. 2.6 kmol of NaOH, and also further water, namely 445 kg. Since the stoichiometric amount of NaOH is 3.45 kmol, the 2.6 kmol of NaOH metered into the first stirred vessel represents only 75 mol % of the stoichiometrically necessary amount, corresponding to a stoichiometric alkali deficiency of 0.85 kmol or 25 mol %. 80%, i.e. 0.7 kmol of NaOH, of the remaining amount of alkali, 0.85 kmol, lacking in the first stirred vessel was fed continuously per hour to the second stirred vessel and the remaining amount still lacking in the second stirred vessel compared to the stoichiometric amount of NaOH was fed continuously per hour to the third stirred vessel.

A temperature of 30° to 35° C. was maintained in the first stirred vessel, a temperature of 40° to 45° C. in the second vessel and a temperature of 55° to 60° C. in the third vessel (a pressure of about 2.0 bar was present in the first vessel, a pressure of about 1.5 bar was present in the second vessel and a pressure of about 0.5 bar was present in the third vessel).

The mean residence time over the three stirred vessels was 16 hours.

The product (product mixture) leaving the first vessel contained 5 mol % of free amine, the product leaving the second vessel contained 1 mol % and the product leaving the third vessel contained 0.5 mol %, mol percentages being related to the dimethylamine employed.

The product leaving the third reaction vessel had an active compound concentration of 65% by weight and was worked up as in Examples 1 to 3.

An aqueous solution which was free of contaminants and which had a DADMAC content of 70% by weight and a sodium chloride content of 1.5% by weight was obtained.

EXAMPLE 6

The reaction was carried out in the three reaction vessels of Example 4 arranged in the form of a cascade.

Per hour, the following were fed continuously into the first stirred vessel: 397 kg (5.2 kmol) of allyl chloride, 117 kg (2.6 kmol) of dimethylamine and 177 kg of 50% strength by weight aqueous sodium hydroxide solution, i.e. 2.2 kmol of NaOH, and also further water, namely 268 kg. Since the stoichiometric amount of NaOH is 2.6 kmol, the 2.2 kmol of NaOH metered into the first stirred vessel represents only 85 mol % of the stoichiometrically necessary amount, corresponding to a stoichiometric alkali deficiency of 0.4 kmol or 15 mol %. Of the remaining amount of alkali, 0.4 kmol, lacking in the first stirred vessel, 80%, i.e. 0.32 kmol of NaOH, were fed continuously per hour to the second stirred vessel and the remaining amount still lacking in the second stirred vessel related to the stoichiometric amount of NaOH was fed continuously per hour to the third reaction vessel.

A temperature of 40° to 45° C. was maintained in the first stirred vessel, a temperature of 50° to 55° C. in the second stirred vessel and a temperature of 50° to 55° C. in the third vessel (a pressure of about 1.5 bar was present in the first vessel, a pressure of about 1.0 bar was present in the second vessel and a pressure of about 0.5 bar was present in the third vessel). The mean residence time over the three stirred vessels was 24 hours.

The product (product mixture) leaving the first vessel contained 0.5 mol % of free amine, the product leaving the second vessel contained 0.1 mol % and the product leaving the third vessel contained 0.05 mol %, mol percentages being related to the dimethylamine employed. The product leaving the third reaction vessel had an active compound concentration of 68% by weight and was worked up as in Examples 1 to 3.

An aqueous solution which was free of contaminants and which had a DADMAC content of 70% by weight and a sodium chloride content of 1.5% by weight was obtained.

EXAMPLE 7

The reaction was carried out in the three reaction vessels of Example 4 arranged in the form of a cascade.

Per hour, the following were fed continuously into the first stirred vessel: 397 kg (5.2 kmol) of allyl chloride, 117 kg (2.6 kmol) of dimethylamine and 234 kg 40% strength by weight aqueous sodium hydroxide solution, i.e. 2.34 kmol of NaOH, and also further water, namely 293 kg. Since the stoichiometric amount of NaOH is 2.6 kmol, the 2.34 kmol of NaOH metered into the first stirred vessel represents only 90 mol % of the stoichiometrically necessary amount, corresponding to a stoichiometric alkali deficiency of 0.26 kmol or 10 mol %. Of the remaining amount of alkali, 0.26 kmol, lacking in the first stirred vessel, 95%, i.e. 0.25 kmol of NaOH, were fed continuously per hour to the second stirred vessel and the remaining amount still lacking in the second stirred vessel related to the stoichiometric amount of NaOH was fed continuously per hour to the third reaction vessel.

A temperature of 55° to 60° C. was maintained in the first stirred vessel, a temperature of 55° to 60° C. in the second vessel and a temperature of 55° to 60° C. in the third vessel also (a pressure of about 1.5 bar was present in the first vessel, a pressure of about 1.0 bar was present in the second vessel and a pressure of about 0.5 bar was present in the third vessel).

The mean residence time over the three stirred vessels was 22 hours.

The product (product mixture) leaving the first vessel contained 0.5 mol % of free amine, the product leaving the second vessel contained 0.2 mol % and the product leaving the third vessel contained 0.1 mol %, mol percentages being related to the dimethylamine employed.

The product leaving the third reaction vessel had an active compound concentration of 68% by weight and was worked up as in Examples 1 to 3.

An aqueous solution which was free of contaminants and which had a DADMAC content of 70% by weight and a sodium chloride content of 1.5% by weight was obtained.

We claim:

1. A continuous process for the preparation of dimethyldiallylammonium chloride by reaction, with stirring, of dimethylamine, allyl chloride and alkali metal hydroxide which is dissolved in water, which comprises carrying out the reaction in at least two stirred vessels arranged in the form of a cascade, proceeding in such a manner that
   (a) dimethylamine and allyl chloride in the stoichiometric amount in each case and only 60 to 95 mol % of the stoichiometrically necessary amount of alkali metal hydroxide are fed simultaneously and continuously to the first stirred vessel, and, at a temperature of 20° to 70° C. and at the pressure produced, a residence time is set in this vessel such that the product leaving the vessel still contains at most 10 mol % of free amine, relative to the molar amount of dimethylamine employed,
   (b) the remaining amount of alkali metal hydroxide which is lacking in the first stirred vessel compared to the stoichiometric amount is fed continuously to the stirred vessels succeeding the first vessel and, at a temperature which is in the range from 20° to 70° C. and which is up to 30° C. higher than in the respective previous vessel and at the pressure produced, a residence time is set in each of these vessels such that the product leaving the vessel still contains at most 2 mol % of free amine in each case, relative to the molar amount of dimethylamine employed, this amount of free amine being held the same or smaller from vessel to vessel in the case of several subsequent stirred vessels, and
   (c) the desired dimethyldiallylammonium chloride is recovered from the product leaving the stirred vessel cascade.

2. The process as claimed in claim 1, wherein the same temperature as in the first stirred vessel or a temperature which is up to 30° C. higher than in the first stirred vessel is maintained in the subsequent stirred vessels, the temperature from vessel to vessel being the same or increasing in essentially identical amounts in the case of several subsequent stirred vessels.

3. The process as claimed in claim 1, wherein a temperature of 30° to 50° C. is maintained in the first stirred vessel and a temperature of 50° to 60° C. is maintained in the stirred vessels succeeding the first stirred vessel, the temperature from vessel to vessel being the same or increasing in essentially identical amounts in the case of several subsequent stirred vessels.

4. The process as claimed in claim 1, wherein the remaining amount of alkali metal hydroxide lacking in the first stirred vessel in comparison to the stoichiometric amount is fed to the stirred vessels succeeding the first stirred vessel in portions which decrease from vessel to vessel.

5. The process as claimed in claim 1, wherein the reaction is carried out in two or three stirred vessels arranged in the form of a cascade.

6. The process as claimed in claim 1, wherein the reaction is carried out in two or three stirred vessels arranged in the form of a cascade, proceeding in such a manner that only 70 to 90 mol % of the stoichiometrically necessary amount of alkali metal hydroxide is fed to the first stirred vessel and, at a temperature of 30° to 50° C. and at the pressure produced, a residence time is set in this vessel such that the product leaving the vessel still contains 0.05 to 10 mol % of free amine, and, at a temperature of 50° to 60° C. and at the pressure produced, a residence time is set in each of the stirred vessels succeeding the first stirred vessel such that the product leaving the vessel still contains 0.05 to 2 mol % of free amine in each case, the same temperature or a higher temperature being maintained in the third vessel as in the second vessel in the case of three stirred vessels and, of the remaining amount of alkali metal hydroxide lacking in the first stirred vessel, 70 to 95 mol % of this remaining amount being fed to the second vessel and the remaining amount still lacking in the second vessel related to the stoichiometric amount of alkali metal hydroxide being fed to the third vessel.

* * * * *